United States Patent [19]
Zelle et al.

[11] Patent Number: 5,811,434
[45] Date of Patent: Sep. 22, 1998

[54] METHODS AND COMPOSITIONS FOR STIMULATING NEURITE GROWTH

[75] Inventors: Robert E. Zelle, Stow; Michael Su, Newton, both of Mass.

[73] Assignee: Vertex Pharmacueticals Incorporated, Cambridge, Mass.

[21] Appl. No.: 748,448

[22] Filed: Nov. 13, 1996

[51] Int. Cl.$^6$ ........................ C07D 211/60; A61K 31/215
[52] U.S. Cl. .................. 514/307; 514/314; 514/315; 514/318; 514/330; 514/332; 514/351; 514/237.2; 546/139; 546/192; 546/193; 546/194; 546/245; 546/256; 546/300; 544/129
[58] Field of Search ................ 544/129; 546/153, 546/192, 193, 194, 245, 139, 256, 300; 514/251.2, 314, 315, 318, 330, 307, 332, 351

[56] References Cited

U.S. PATENT DOCUMENTS

| 5,192,773 | 3/1993 | Armistead et al. | 514/315 |
|---|---|---|---|
| 5,543,423 | 8/1996 | Zelle et al. | 514/332 |
| 5,614,547 | 3/1997 | Hamilton et al. | 514/423 |
| 5,696,135 | 12/1997 | Steiner et al. | 514/317 |

FOREIGN PATENT DOCUMENTS

| 9200278 | 1/1992 | WIPO | 514/315 |
|---|---|---|---|
| WO 96/15101 | 5/1995 | WIPO . | |
| WO 96/40140 | 12/1996 | WIPO . | |
| WO 96/40633 | 12/1996 | WIPO . | |
| WO 97/16190 | 5/1997 | WIPO . | |

OTHER PUBLICATIONS

J.P. Steiner et al., "High brain densities of the immunophilin FKBP colocalized with calcineurin," *Nature*, 358, pp. 584–587 (1992).

J.R. Hauske et al., "Design and synthesis of novel FKBP inhibitors," *J. Med. Chem.*, 35, pp. 4284–4296 (1992).

B.G. Gold et al., "FK506, an immunosuppressant, increases functional recovery and axonal regeneration in the rat following axotomy of the sciatic nerve," *Soc. Neurosci. Abs.*, 19, p. 1316 (1993).

B.G. Gold et al., "The immunosuppressant FK506 increases the Rate of Axonal Regeneration in Rat Sciatic Nerve," *J. Neuroscience*, 15(11), pp. 7509–7516 (Nov. 1995).

W.E. Lyons et al., "Immunosupressant FK506 promotes neurite outgrowth in cultures of PC12 cells and sensory ganglia," *Proc. Natl. Acad. Sci. USA*, 91, pp. 3191–3195 (Apr., 1994).

John Sharkey et al., "Immunophilins mediate the neuroprotective effects of FK506 of focal cerebral ischaemia." *Nature*, 371, pp. 336–339 (Sep. 22, 1994).

W.E. Lyons et al., "Neuronal regeneration enhances the expression of the immunophilin FKBP–12," *J. Neuroscience.*, 15, pp. 2985–2994 (Apr., 1995).

*Primary Examiner*—Zinna Northington Davis
*Attorney, Agent, or Firm*—Fish & Neave; James F. Haley, Jr.; N. Gouindaswamy

[57] ABSTRACT

The present invention relates to methods and pharmaceutical compositions for stimulating the growth of neurites in nerve cells. The compositions comprise a neurotrophic amount of a compound and a neurotrophic factor, such as nerve growth factor (NGF). The methods comprise treating nerve cells with the above compositions or compositions comprising the compound without a neurotropic factor. The methods of this invention can be used to promote repair of neuronal damage caused by disease or physical trauma.

31 Claims, No Drawings

METHODS AND COMPOSITIONS FOR STIMULATING NEURITE GROWTH

TECHNICAL FIELD OF THE INVENTION

The present invention relates to methods and pharmaceutical compositions for stimulating the growth of neurites in nerve cells. The compositions comprise a neurotrophic amount of a compound and a neurotrophic factor, such as nerve growth factor (NGF). The methods comprise treating nerve cells with the above compositions or compositions comprising the compound without a neurotropic factor. The methods of this invention can be used to promote repair of neuronal damage caused by disease or physical trauma.

BACKGROUND OF THE INVENTION

Neurological diseases are associated with the death or injury of neuronal cells. The loss of dopaminergic neurons in the substantia nigra is the etiological cause for Parkinson's disease. Although the molecular mechanism of neurodegeneration in Alzheimer's disease is yet to be established, it is clear that brain inflammation, and deposition of beta-amyloid protein and other such agents may inhibit the survival of neurons and mitigate the growth of neurites used for communication between neurons. In patients suffering from brain ischemia or spinal cord injuries, extensive neuronal cell death is observed. Currently, there are no satisfactory treatments for these diseases.

Typical treatment of neurological diseases involves drugs capable of inhibiting neuronal cell death. A more recent approach involves the promotion of nerve regeneration by promoting neurite outgrowth.

Neurite outgrowth, which is critical for the survival of neurons, is stimulated in vitro by nerve growth factors (NGF). For example, Glial Cell Line-Derived Neurotrophic Factor (GDNF) demonstrates neurotrophic activity both, in vivo and in vitro, and is currently being investigated for the treatment of Parkinson's disease. Insulin and Insulin-like growth factors have been shown to stimulate growth of neurites in rat pheochromocytoma PC12 cells and in cultured sympathetic and sensory neurons [Recio-Pinto et al., *J. Neurosci.*, 6, pp. 1211–1219 (1986)]. Insulin and Insulin-like growth factors also stimulate the regeneration of injured motor nerves in vivo and in vitro [Near et al., *PNAS*, pp. 89, 11716–11720 (1992); and Edbladh et al., *Brain Res.*, 641, pp. 76–82 (1994)]. Similarly, fibroblast growth factor (FGF) stimulates neural proliferation [D. Gospodarowicz et al., *Cell Differ.*, 19, p. 1 (1986)] and growth [M. A. Walter et al., *Lymphokine Cytokine Res.*, 12, p. 135 (1993)].

There are, however, several disadvantages associated with the use of nerve growth factors for treating neurological diseases. They do not readily cross the blood-brain barrier. They are unstable in plasma. And they have poor drug delivery properties.

Recently, small molecules have been shown to stimulate neurite outgrowth in vivo. In individuals suffering from a neurological disease, this stimulation of neurite outgrowth protects neurons from further degeneration, and accelerates the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.*, 56, pp. 169–78 (1996); and B. S. McEwen et al., *Brain Res. Dev. Brain. Res.*, 87, pp. 91–95 (1995)]. The progress of Alzheimer's disease is slowed in women who take estrogen. Estrogen is hypothesized to complement NGF and other neurotrophins and thereby help neurons differentiate and survive.

Tacrolimus, an immunosuppressive drug, has been demonstrated to act synergistically with NGF in stimulating neurite outgrowth in PC12 cells as well as sensory ganglia [Lyons et al., *PNAS*, 91, pp. 3191–3195 (1994)]. This compound has also been shown to be neuroprotective in focal cerebral ischemia [J. Sharkey and S. P. Butcher, *Nature*, 371, pp.336–339 (1994)] and to increase the rate of axonal regeneration in injured sciatic nerve [Gold et al., *J. Neurosci.*, 15, pp. 7509–16 (1995)].

Though a wide variety of neurological degenerative disorders may be treated by stimulating neurite outgrowth, there are relatively few agents known to possess these properties. Thus, there remains a great need for new pharmaceutically acceptable compounds and compositions that have the ability to stimulate neurite outgrowth in patients.

SUMMARY OF THE INVENTION

Applicants have solved the above problem by discovering that compounds previously invented by one of the co-applicants for use in reversing multi-drug resistance also surprisingly and unexpectedly possess neurotropic activity.

These compounds stimulate neurite outgrowth in the presence of exogenous or endogenous NGF. The compositions disclosed herein comprise a compound from the genera described above and a neuronal growth factor. The methods to stimulate neurite outgrowth disclosed herein employ the above amino acid derivatives either alone or in combination with a neuronal growth factor. The methods are useful in treating nerve damage caused by various neurological diseases and physical traumas and also in ex vivo nerve regeneration.

DETAILED DESCRIPTION OF THE INVENTION

The present invention provides pharmaceutical compositions which comprise three components. The first component is a compound having the formula (I):

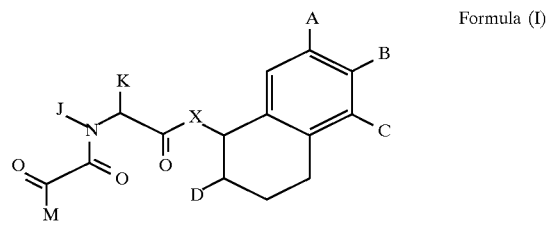

Formula (I)

and pharmaceutically acceptable derivatives thereof, wherein A, B and C are independently selected from hydrogen, (C1–C6)-straight or branched alkyl, O—(C1–C6)-straight or branced alkyl, $(CH_2)_n Ar$, $Y (CH_2)_n$-Ar, or halogen; wherein n=0–4;

wherein Y=O, S, or $NR_1$, where $R_1$=(C1–C6)-straight or branched alkyl or hydrogen;

wherein each Ar is selected from phenyl, 1-naphthyl, 2-naphthyl, indenyl, azulenyl, fluorenyl and anthracenyl, 2-furyl, 3-furyl, 2-thienyl, 3-thienyl,2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-isoquinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl;

wherein Ar optionally contains one to three substituents independently selected from hydrogen, hydroxyl, halogen, nitro, SO$_3$H, trifluoromethyl, trifluoromethoxy, (C1–C6)-straight or branched alkyl, O—(C1–C6)-straight or branched alkyl, O-benzyl, O-phenyl, 1,2-methylenedioxy, carboxyl, morpholinyl, piperidinyl, NR$_2$R$_3$, or NR$_2$R$_3$ carboxamides, wherein R$_2$ and R$_3$ are independently selected from hydrogen, (C1–C5)-straight or branched alkyl or benzyl;

wherein D is selected from hydrogen or (CH$_2$)$_m$—E; where E is Ar or NR$_4$R$_5$; where m=1–3, and each of R$_4$ and R$_5$ are independently selected from hydrogen, alkyl (C1–C5 straight or branched), or (CH$_2$)Ar or can be taken together to form a 5 or 6 membered heterocyclic ring.

wherein X is O or NR$_6$; where R6 is is selected from hydrogen, (C1–C6)-straight or branched alkyl or (CH$_2$)$_m$—Ar, where m=1–3;

wherein J and K are independently (C1–C6)-straight or branched alkyl or Ar-substituted with (C1–C6)-straight or branched alkyl or wherein J and K are taken together to form a five or six membered ring or a five or six membered benzo-fused ring;

wherein M is (C1–C6)-straight or branched alkyl or Ar;

wherein the stereochemistry at carbon 1 and carbon 2 is independently R or S.

As defined herein, the compounds of this invention include all optical and racemic isomers.

A "pharmaceutically acceptable derivative," as used herein denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote or augment neurite outgrowth.

According to a preferred embodiment, the pharmaceutical compositions of the present invention comprise a compound having formula (II):

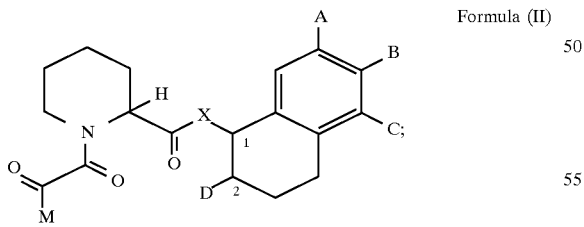

Formula (II)

and pharmaceutically acceptable derivatives thereof, wherein M, X, A, B, C, and D are as defined above.

According to another preferred embodiment, the pharmaceutical compositions of the present invention comprise a compound having formula (III):

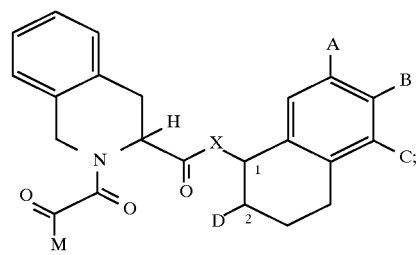

Formula (III)

and pharmaceutically acceptable derivatives thereof, wherein M, X, A, B, C, and D are as defined above.

According to yet another preferred embodiment, the pharmaceutical compositions of the present invention comprise a compound having formula (IV):

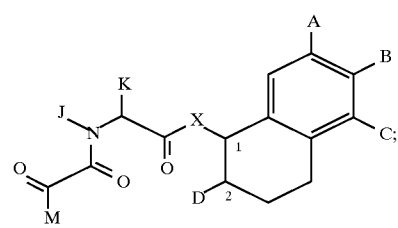

Formula (IV)

and pharmaceutically acceptable derivatives thereof, wherein M, X, A, B, C, and D are as defined above;

J is methyl or hydrogen; and

K is (CH$_2$)$_m$—Ar or (C1–C6)-straight or branched alkyl. More preferably, in compound of formula (IV), K is substituted or unsubstituted benzyl. Most preferably, K is benzyl or 4-halobenzyl in compound of formula (IV).

Examples of pharmaceutical compounds within the scope of formula (I) of the present invention are indicated in Table 1, below.

TABLE I

| Cpd | A | B | C | D | J | K | X |
|---|---|---|---|---|---|---|---|
| 6 | OCH$_2$-4Pyr | H | H | H | | | O |
| 7 | OCH$_2$-4Pyr | H | H | H | | | O |
| 9 | H | H | OCH$_2$-4Pyr | H | | | O |
| 11A | OCH$_2$-4Pyr | H | H | H | | | NH |

TABLE I-continued

| Cpd | A | B | C | D | J | K | X |
|---|---|---|---|---|---|---|---|
| 11B | OCH$_2$-4Pyr | H | H | H | | | NH |
| 15 | OCH$_2$-4Pyr | H | H | H | | | N-benzyl |
| 16 | OCH$_2$-4Pyr | H | H | H | | | N-benzyl |
| 17 | OCH$_2$-4Pyr | H | H | H | | | O |
| 18 | OCH$_2$-4Pyr | H | H | H | | | O |
| 19 | OCH$_2$-4Pyr | H | H | H | H | benzyl | O |
| 20 | OCH$_2$-4Pyr | H | H | H | CH3 | benzyl | O |
| 21 | OCH$_2$-4Pyr | H | H | H | CH3 | benzyl | O |
| 29A | O-propyl | methyl | O-propyl | (CH$_2$)-3-Pyr | | | O |
| 29B | O-propyl | methyl | O-propyl | (CH$_2$)-3-Pyr | | | O |
| 30A | O-propyl | metthyl | O-propyl | (CH$_2$)-3-Pyr | | | O |
| 30B | O-propyl | methyl | O-propyl | (CH$_2$)-3-Pyr | | | O |

If pharmaceutically acceptable salts of the compounds are used, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenyl-propionate, picrate, pivalate, propionate, succinate, tartarate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The second component in each of the pharmaceutical compositions described above is a neurotrophic factor. The term "neurotrophic factor", as used herein, refers to compounds which are capable of stimulating growth or proliferation of nervous tissue. As used in this application, the term "neurotrophic factor" excludes the compounds described herein.

Numerous neurotrophic factors have been identified in the art and any of those factors may be utilized in the compositions of this invention. These neurotrophic factors include, but are not limited to, nerve growth factor (NGF), insulin growth factor (IGF-1) and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3) and neurotrophin 4/5 (NT-4/5). The most preferred neurotrophic factor in the compositions of this invention is NGF.

The third component of the pharmaceutically acceptable compositions of this invention is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both, the compound and the neurotrophic factor that may be combined with the carrier materials to produce a single dosage form will vary depending upon the host treated, the particular mode of administration. The two active ingredients of the pharmaceutical compositions of this invention act synergistically to stimulate neurite outgrowth. Therefore, the amount of neurotrophic factor in such compositions will be less than that required in a monotherapy utilizing only that factor. Preferably, the compositions should be formulated so that a dosage of between 0.01–100 mg/kg body weight/day of the compound can be administered and a dosage of between 0.01–100 $\mu$g/kg body weight/day of the neurotrophic can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and neurotrophic factor in the composition.

According to another embodiment, this invention provides methods for stimulating neurite outgrowth. In one aspect of this embodiment, the method is used to stimulate neurite outgrowth in a patient and is achieved by administering to the patient a pharmaceutically acceptable composition comprising any of the compounds described above and a pharmaceutically acceptable carrier. The amount of compound utilized in these methods is between about 0.01 and 100 mg/kg body weight/day.

In another aspect of this embodiment, the method is used to stimulate nerve growth ex vivo. For this aspect, the compounds described above can be applied directly to the nerve cells in culture. This aspect of the invention is useful for ex vivo nerve regeneration.

According to an alternate embodiment, the method of stimulating neurite outgrowth comprises the additional step of treating a patient or ex vivo nerve cells in culture with a neurotrophic factor, such as those contained in the pharmaceutical compositions of this invention described above. This embodiment includes administering the compound and the neurotrophic agent in a single dosage form or in separate, multiple dosage forms when they are to be administered to a patient. If separate dosage forms are utilized, they may be administered concurrently, consecutively or within less than about 5 hours of one another.

The methods and compositions of this invention may be used to treat nerve damage caused by a wide variety of diseases or physical traumas. These include, but are not limited to, Alzheimer's disease, Parkinson's disease, ALS, multiple sclerosis, stroke and ischemia associated with stroke, neural paropathy, other neural degenerative diseases, motor neuron diseases, sciatic crush, peripheral neuropathy, particularly neuropathy associated with diabetes, spinal cord injuries and facial nerve crush.

In order that the invention described herein may be more fully understood, the following examples are set forth. It should be understood that these examples are for illustrative purposes only and are not to be construed as limiting this invention in any manner.

EXAMPLES

General Methods

Proton nuclear magnetic resonance ($^1$H NMR) spectra were recorded at 500 MHz on a Bruker AMX 500. Chemical shifts are reported in parts per million ($\delta$) relative to Me$_4$Si ($\delta$ 0.0). Analytical high performance liquid chromatography was performed on either a Waters 600E or a Hewlett Packard 1050 liquid chromatograph.

Example 1

7-(Pyridin-4-ylmethoxy)-1,2,3,4-tetrahydronaphthalen-1-one (Compound 1):

To a solution of 7-hydroxy-1-tetralone (15.0 g, 92.59 mmol) in dimethylsulfoxide (150 mL) was added in portions powdered potassium carbonate (30.66 g, 0.11 mol) followed by the addition of 4-picoyl chloride hydrochloroide (18.22 g, 0.22 mol). The resulting mixture was heated at 50° C. for 30 min. The resulting dark brown mixture was diluted with water (200 mL) and extracted with ethyl acetate (500 mL). The aqueous phase was re-extracted with ethyl acetate (300 mL) and the extracts combined, dried over anh. magnesium sulfate, filtered and concentrated in vacuo. Chromatography of the residue on silica gel (elution with 40–60% ethyl acetate: hexanes) provided 20.82 g of Compound 1 as an oil which crystallized upon standing.

Example 2

7-(Pyridin-4-ylmethoxy)-1,2,3,4-tetrahydronaphthalen-1-ol (Compound 2):

To a solution of Compound 1 (16.41 g, 64.9 mmol) in tetrahydrofuran (75 mL) at 0° C. was added dropwise a 1M solution of diisobutylaluminum hydride in toluene (97.3 mL). After 1 hr, the reaction was quenched with aqueous potassium sodium tartrate and diluted with ethyl acetate followed by warming to room temperature. After stirring for an additional hour, the layers were separated and the aqueous phase was re-extracted with ethyl acetate (2×). The extracts were combined, washed with brine, dried over anh. magnesium sulfate, filtered and concentrated in vacuo. Chromatography of the residue on silica gel (elution with ethyl acetate) provided 12.96 g of Compound 2 as an oil which crystallized upon standing.

Examples 2 (S) and 3 (R)

7-(Pyridin-4-ylmethoxy)-1,2,3,4-tetrahydronaphthalen-1(S)-ol (Compound 2 (S)) and 1(R)-Acetoxy-7-(Pyridin-4-ylmethoxy)-1,2,3,4-tetrahydronaphthalene (Compound 3 (R)):

A solution of Compound 2 (12.96, 50.82 mmol) in in tetrahydrofuran (20 mL) was diluted with tert-butylmethyl ether (260 mL) followed by the addition of vinyl acetate (19.1 mL, 0.21 mol) and Amano PS-30 Lipase (13.0 g). After stirring for 8 hrs, the reaction was filtered and concentrated in vacuo to provide an oil. Chromatography on silica gel (elution with 20% acetone:hexanes) provided 7.41 g of acetate 3(R) as a white crystalline material. Further elution with 60% acetone:hexanes provided 6.1 g of Compound 2(S) as a white cyrstalline material. The enantiomeric purity of compound 2(S) was established by HPLC using a Chiralpak OD column to be >99.8% ee.

Example 2(R)

7-(Pyridin-4-ylmethoxy)-1,2,3,4-tetrahydronaphthalen-1(R)-ol (Compound 2 (R))

To a solution of Compound 3(R) (6.1 g, 20.9 mmol) in methanol (35 mL) was added powdered potassium carbonate (2.88 g, 20.9 mmol). After stirring for 45 min, the reaction was concentrated in vacuo. The residue was taken-up into methylene chloride and 50% brine. The layers were separated and the aqueous phase re-extracted with methylene chloride. The organics were combined, washed with brine, dried over anh. magnesium sulfate, filtered and concentrated in vacuo to provide 4.7 g of Compound 2(R) as a white crystalline material. The enantiomeric purity of compound 2(S) was established by HPLC using a Chiralpak OD column to be >99.4% ee.

Example 4

(S)-Piperidine-1,2-dicarboxylic acid 1-allyl ester (2-(7-pyridin-4-ylmethoxy)-1,2,3,4-tetrahydronaphthalen-1-yl) ester (Compound 4):

To a solution of Compound 2 (663 mg, 2.6 mmol), Alloc-(S)-pipecolic acid (610 mg, 2.86 mmol) and dimethylaminopyridine (32 mg, 0.26 mmol), in methylene chloride (5 mL) was added (3-dimethylaminopropyl)-3-ethyl-carbodiimide hydrochloride (548 mg, 2.86 mmol). After stirring for 24 hr, the reaction was diluted with ethyl acetate and water. The layers were separated and the aqueous phase was re-extracted with ethyl acetate. The extracts were combined, washed with sat. sodium bicarbonate, water, brine, dried over anh. magnesium sulfate, filtered and concentrated in vacuo. Chromatography of the residue on silica gel (elution with 20% acetone:hexanes) provided 940 mg of Compound 4 as a mixture of diastereomers.

Example 5

(S)-Piperidine-2-carboxylic acid (2-(7-pyridin-4-ylmethoxy)-1,2,3,4-tetrahydronaphthalen-1-yl) ester (Compound 5):

To a solution of Compound 4 (940 mg, 2.09 mmol) in tetrahydrofuran (5.0 mL)was added morpholine (1.1 mL, 12.6 mmol) and tetrakistriphenylphosphine pallidiun (0) (241 mg, 0.21 mmol). After 1 hr, the heterogenous mixture was diluted with ethyl acetate, washed with 50% brine, 5% sodium bicarbonate, brine, dried over anh. magnesium sulfate, filtered and concentrated in vacuo. Chromatography of the residue on silica gel (elution with 50–100% acetone:hexanes) provided 510 mg of Compound 5.

Examples 6 and 7

1-(2-Oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl) ester (Compound 6) and 1-(2-Oxo-2(3,4,5-trimethoxyphenyl)-acetyl)-piperidine-2(S)-carboxylic acid 2-((7-pyridin-4-yl methoxy)-1,2,3,4-tetrahydronaphthalen-1(R)-yl) ester (Compound 7):

To a solution of Compound 5 (510 mg, 1.4 mmol) and 3,4,5-trimethoxybenzyolformic acid (505 mg, 2.1 mmol) in methylene chloride (6 mL) was added (3-dimethylaminopropyl)-3-ethyl-carbodiimide hydrochloride (400 mg, 2.1 mmol). After stirring for 24 hr, the reaction was diluted with ethyl acetate and water. The layers were separated and the aqueous phase was re-extracted with ethyl acetate. The extracts were combined, washed with sat. sodium bicarbonate, water, brine, dried over anh. magnesium sulfate, filtered and concentrated in vacuo. Chromatography of the residue on silica gel (elution with 25% acetone:hexanes) provided 558 mg of product as a mixture of diastereomers. Reverse phase MPLC provided diastereomerically pure Compound 6 and Compound 7.

Alternatively, replacement of Compound 2 with resolved Compound 2(S) in Examples 4–5 and the above example provided Compound 6 directly, whereas Compound 2(R) provided Compound 7. Compound 6: $^1$H NMR as a mixture of rotomers (500 MHz, CDCl$_3$) d 8.53 (d), 8.55(d), 7.38 (s), 7.34–7.28 (m), 7.17 (s), 7.05 (d), 7.01 (d), 6.88–6.79 (m), 6.64 (d) 6.00 (t), 5.93 (t), 5.39 (br d), 5.05–5.00 (m), 4.58 (br d), 4.34 (br d), 3.93–3.88 (m), 3.79 (s), 3.49 (br d), 3.28 (dt), 3.02 (dt), 2.80 (dt), 2.73–2.60 (m), 2.36–2.28 (m), 2.08–1.49 (m), 1.37–1.27 (m).

Compound 7: $^1$H NMR as a mixture of rotomers (500 MHz, CDCl$_3$) d 8.56–8.54 (m), 7.35 (s), 7.29–7.28 (m), 7.16 (s), 7.05 (d), 7.00 (d), 6.86–6.81 (m), 6.73 (d), 6.00 (t), 5.87 (t), 5.35 (br d), 5.07–4.93 (m), 4.58 (br d), 4.34 (m), 3.94–3.89 (m), 3.84 (s), 3.45 (br d), 3.22 (dt), 3.09 (dt), 2.79 (dt), 2.72–2.60 (m), 2.25 (m), 2.10 (m), 2.03–1.47 (m), 1.40–1.30 (m), 1.27–1.17 (m).

Example 8

1-(2-Oxo-2-(3,4,5-trimethoxyphenyl)-acetyl)-piperidine-2(S)-carboxylic acid 2-((6-pyridin-4-ylmethoxy)-1,2,3,4-tetrahydronaphthalen-1-yl) ester (Compound 8)

Compound 8 was prepared as described in Examples 1–2 and 4–6 utilizing 6-hydroxy-1-tetralone in place of 7-hydroxy-1-tetralone to provide Compound 8 as a mixture of diastereomers. $^1$H NMR as a mixture of diastereomers and rotomers (500 MHz, CDCl$_3$) d 8.59 (d), 7.38 (s), 7.37 (s), 7.33 (m), 7.22 (d), 7.18 (dd), 7.04 (d), 6.77 (dt), 6.70 (m), 6.64 (m), 6.04 (m), 5.92 (t), 5.88 (t), 5.35 (m), 5.06 (s), 5.05 (s), 5.03 (s), 4.58 (m), 4.31 (dd), 3.94 (s), 3.93 (s), 3.92 (s), 3.87 (s), 3.86 (s), 3.47 (br d), 3.27 (dq), 3.13 (dt), 3.07 (dt), 2.87–2.61 (m), 2.34 (br d), 2.26 (br d), 2.18–1.18 (m).

Example 9

1-(2-Oxo-2-(3,4,5-trimethoxyphenyl)-acetyl)-piperidine-2(S)-carboxylic acid 2-((5-pyridin-4-ylmethoxy)-1,2,3,4-tetrahydronaphthalen-1-yl) ester (Compound 9)

Compound 9 was prepared as described in Examples 1–2 and 4–6 utilizing 5-hydroxy-1-tetralone in place of 7-hydroxy-1-tetralone to provide Compound 9 as a mixture of diastereomers. $^1$H NMR as a mixture of diastereomers and rotomers (500 MHz, CDCl$_3$) d 8.64 (m), 7.39 (m), 7.27 (s), 7.20 (d), 7.17 (q), 6.98 (d), 6.92 (d), 6.80 (t), 6.73 (dd), 6.40 (d), 6.10 (q), 5.99 (t), 5.95 (t), 5.40 (m), 5.12 (m), 5.12 (s), 5.08 (s), 4.60 (m), 4.35 (m), 3.96 (s), 3.85 (s), 3.94E(s), 3.90 (s), 3.89 (s), 3.50 (br d), 3.30 (dq), 3.19–3.08 (m), 3.0–2.86 (m), 2.74–2.58 (m), 2.38 (m), 2.30 (m), 2.10–1.50 (m), 1.45–1.25 (m).

Example 10

1-Amino-7-(pyridin-4-ylmethoxy)-1,2,3,4 tetrahydronaphthalene (Compound 10):

To a solution of Compound 1 (1.71 g, 6.75 mmol) and methoxyamine hydrochloride (845 mg, 10.12 mmol) in abs. ethanol (20 mL) was added powdered potassium carbonate (2.25 g, 16.88 mmol) and the reaction heated to reflux. After 2 hr, the reaction was cooled and concentrated in vacuo. The residue was diluted with ethyl acetate, washed with 5% sodium bicarbonate, water, brine, dried over anh. magnesium sulfate, filtered and concentrated in vacuo. Chromatography of the residue on silica gel (elution with 40% ethyl acetate:hexanes) provided 1.9 g of oxime.

To a solution of the above oxime in tetrahydrofuran (5 mL) was added a 1M solution of borane in tetrahydrofuran (20.25 mL) and the reaction heated to reflux and stirred for 18 hr. The reaction was cooled and quenched with saturated methanolic hydrochloric acid (20 mL) and the reaction reheated to reflux and stirred an additional 30 min. The reaction was cooled and concentrated to dryness. The residue was taken up into water (10 mL) and washed with diethyl ether (3× 20 mL). The aqueous phase was adjusted to pH 8.0 with sat. sodium bicarbonate and extracted with ethyl acetate (3× 50 mL).

The extracts were combined, washed with brine, dried over anh. magnesium sulfate, filtered and concentrated in vacuo to provide 945 mg of Compound 10.

Example 11A and 11B 1-(2-Oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(R)-yl) amide and 1-(2-Oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl) amide (Compound 11 A and 11B):

Compounds 11A and 11B were prepared as described in Example 4–6 by replacing Compound 2 with Compound 10 to provide a mixture of diastereromers. Chromatography of the residue on silica gel (elution with 20% acetone:hexanes) provided Compound 11A. Further elution provided Compound 11B.

Compound 11A: $^1$H NMR as a mixture of diastereomers and rotomers (500 MHz, CDCl$_3$) d 8.57 (m), 7.36(d), 7.34 (s), 7.30 (d), 7.13 (s), 7.02 (t), 6.97 (d), 6.82 (dd), 6.79 (dd), 6.73 (d), 6.11 (d), 5.21 (m), 5.18–5.08 (m), 5.02 (s), 4.66 (br d), 4.18 (d), 3.92 (s), 3.87 (s), 3.81 (s), 3.60 (br d), 3.32 (dt), 2.81–2.64 (m), 2.40 (br d), 2.26 (m), 2.11–2.01 (m), 1.84–1.65 (m), 1.51–1.42 (m).

Compound 11B: $^1$H NMR as a mixture of diastereomers and rotomers (500 MHz, CDCl$_3$) d 8.58 (m), 8.48 (m), 7.34 (s), 7.33 (m), 7.29 (m), 7.21 (d), 7.17 (s), 7.02 (t), 6.86 (d), 6.86–6.76 (m), 6.01 (d), 5.19–5.10 (m), 5.02 (m), 4.99 (q), 4.58 (br d), 4.18 (d), 3.93 (s), 3.89 (s), 3.86 (s), 3.48 (br d), 3.41 (dt), 2.80–2.62 (m), 2.41 (br d), 2.21 (br d), 2.12–2.00 (m), 1.88–1.40 (m).

Example 12

N-Benzyl-1-amino-7-(pyridin-4-ylmethoxy)-1,2, 3,4-tetrahydronaphthalene (Compound 12):

A solution of Compound 1 (820 mg, 3.24 mmol) and benzyl amine (354 L, 3.24 mmol) in benzene (10 mL) was heated to reflux under azeotropic conditions. After the calculated amount of water was collected, the reaction was cooled and concentrated in vacuo. The residue was taken-up into ethanol (5 mL) and added to a slurry of sodium boroydride (246 mg, 6.48 mmol) in ethanol (15 mL). The reaction was heated to 80° C., stirred for 30 min, cooled and concentrated in vacuo. The residue was diluted with ethyl acetate followed by the slow addition of 1N hydrochloric acid. The layers were separated. The aqueous phase was adjusted to pH 7 with 2N sodium hydroxide and extracted with methylene chloride (2×). The organics were combined, washed with brine, dried over anh. magnesium sulfate, filtered and concentrated in vacuo. Chromatography on silica gel (elution with 5% methanol:methylene chloride) provided 1.09 g of Compound 12 as an oil.

Example 13A and 13B (S)-Piperidine-1,2-dicarboxylic acid 1-tert-butyl ester 2(-N-benzyl-(7-pyridin-4-ylmethoxy) -1,2,3,4-tetrahydronaphthalen-1(R)-yl) amide and (S)-Piperidine-1,2-dicarboxylic acid 1-tert-butyl ester 2-(N-benzyl-(7-pyridin-4-ylmethoxy)-1,2,3,4-tetrahydronaphthalen-1(S)-yl) amide (Compound 13A and 13B):

To a solution of Compound 12 (1.09 g, 3.16 mmol) and Boc-(S)-pipecolic acid (868 mg, 3.79 mmol) in methylene chloride (10 mL) was added (3-dimethylaminopropyl)-3-ethyl-carbodiimide hydrochloride (725 mg, 3.79 mmol). After stirring for 72 hr, the reaction was diluted with ethyl acetate and water. The layers were separated and the aqueous phase was re-extracted with ethyl acetate. The extracts were combined, washed with sat. sodium bicarbonate, water, brine, dried over anh. magnesium sulfate, filtered and concentrated in vacuo. Chromatography of the residue on silica gel (elution with 40% acetone:hexanes) provided 601 mg of Compound 13A and further elution provide 181 mg of Compound 13B as white solids.

Example 14

(S)-Piperidine-2-dicarboxylic acid 2-(N-benzyl-(7-pyridin-4-ylmethoxy) -1,2,3,4-tetrahydronaphthalen-1(R)-yl) amide (Compound 14):

To a solution of Compound 13A (601 mg, 1.08 mmol) in methylene chloride (10 mL) was added trifluoroacetic acid (1 mL). After stirring for 1.5 hr, the reaction was concentrated in vacuo. The residue was neutralized with sat. potassium carbonate and extracted with ethyl acetate (2×). The extracts were combined washed with brine, dried over anh. magnesium sulfate, filtered and concentrated in vacuo, to provide 450 mg of Compound 14.

Example 15
1-(2-Oxo-2-(3,4,5-trimethoxyphenyl)-acetyl)-piperidine-2 (S)-carboxylic acid 2-(N-benzyl (7-pyridin-4-ylmethoxy)-1,2,3,4-tetrahydronaphthalen-1-yl) amide (Compound 15):

Compound 15 was prepared according to Example 6, but replacing Compound 5 with 14. $^1$H NMR as a mixture of rotomers (500 MHz, CDCl$_3$) d 8.52 (d), 8.39 (dd), 7.51 (m), 7.44 (s), 7.37 (s), 7.37 (t), 7.30–7.15 (m), 7.09 (d), 7.05 (d), 6.99 (d), 6.89 (dd), 6.74 (m), 6.39 (m), 5.69 (d), 5.41 (m), 5.21 (m), 5.15 (q), 4.90 (q), 4.72 (d), 4.64 (d), 3.95–3.86 (m), 3.70–3.67 (m), 3.57 (br d), 3.54 (d), 3.48 (m), 2.74–2.64 (m), 2.20–1.58 (m).

Example 16
1-(2-Oxo-2-(3,4,5-trimethoxyphenyl)-acetyl)-piperidine-2 (S)-carboxylic acid (2-N-benzyl (7-pyridin-4-ylmethoxy)-1,2,3,4-tetrahydronaphthalen-1-yl) amide (Compound 16):

Compound 16 was prepared according to Example 14–15, but replacing Compound 13A with 13B. $^1$H NMR as a mixture of rotomers (500 MHz, CDCl$_3$) d 8.63 (d), 7.37–7.33 (m), 7.30–7.22 (m), 7.13–7.10 (m), 7.03 (dd), 6.87 (br s), 6.79 (dt), 5.83 (m), 5.06 (q), 4.96 (q), 4.90 (d), 4.83 (q), 4.38 (d), 4.13 (d), 3.94 (s), 3.90 (s), 3.87 (s), 3.85 (s), 2.70–2.62 (m), 2.14 (m), 1.91 (m), 1.88–1.68 (m), 1.54–1.44 (m), 1.35–1.22 (m).

Example 17
2-(2-Oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(R)-yl) ester (Compound 17):

Compound 17 was prepared according to Examples 4–6, but replacing (S)-Alloc-pipecolic acid with (S)-Alloc-3-carboxyl-1,2,3,4-tetrahydroisoquinoline and utilizing Compound 2(R). $^1$H NMR as a mixture of rotomers (500 MHz, CDCl$_3$) d 8.62 (d), 8.54 (d), 7.44 (s), 7.33 (d), 7.27 (d), 7.26–7.08 (m), 7.05 (d), 7.01 (d), 6.98 (d), 6.88–6.78 (m), 6.43 (d), 5.93 (t), 5.77 (t), 5.32 (t), 5.08 (d), 5.02 (q), 4.90 (s), 4.83 (q), 4.67 (d), 4.57 (q), 3.96–3.82 (m), 3.34–3.20 (m), 2.80 (dt), 2.77–2.57 (m), 1.88–1.82 (m), 1.79–1.64 (m).

Example 18
2-(2-Oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(S)-yl) ester (Compound 18):

Compound 18 was prepared according to Examples 4–6, but replacing (S)-Alloc-pipecolic acid with (S)-Alloc-3-carboxyl-1,2,3,4-tetrahydroisoquinoline and utilizing Compound 2(S). $^1$H NMR as a mixture of rotomers (500 MHz, CDCl$_3$) d 8.61 (m), 7.41 (s), 7.40 (s), 7.31–6.96 (m), 6.88–6.80 (m), 6.47 (m), 5.88 (m), 5.74 (m), 5.39 (m), 5.07 (d), 4.87–4.74 (m), 4.60 (q), 3.98–3.82 (m), 3.28–3.18 (m), 2.02–1.62 (m), 1.53–1.45 (m).

Example 19
3-Benzyl-2(S)-((2-oxo-2-(3,4,5-trimethoxyphenyl)acetyl) amino)propanoic acid ((7-pyridin-4-ylmethoxy)-1,2,3,4-tetrahydronaphthalen-1(R)-yl) ester (Compound 19):

Compound 19 was prepared according to Examples 4–6, but replacing (S)-Alloc-pipecolic acid with (S)-Alloc-phenylalanine and utilizing Compound 2(R). $^1$H NMR as a mixture of rotomers (500 MHz, CDCl$_3$) d 8.57 (dd), 7.66(s), 7.52 (d), 7.32–7.23 (m), 7.19 (d), 7.05 (d), 6.87 (m), 6.86 (s), 6.00 (t), 5.03 (q), 4.88 (q), 3.94 (s), 3.88 (s), 3.20 (dq), 2.78 (dt), 2.69–2.63 (m), 1.97–1.73 (m).

Example 20
3-Benzyl-2(S)-(methyl-(2-oxo-2-(3,4,5-trimethoxyphenyl) acetyl)amino)propanoic acid ((7-pyridin-4-ylmethoxy)-1,2,3,4-tetrahydronaphthalen-1(R)-yl) ester (Compound 20):

Compound 20 was prepared according to Examples 4–6, but replacing (S)-Alloc-pipecolic acid with (S)-Alloc-N-methyl-phenylalanine and utilizing Compound 2(R). $^1$H NMR as a mixture of rotomers (500 MHz, CDCl$_3$) d 8.55 (d), 8.52 (d), 7.34 (s), 7.31–7.19 (m), 7.12 (m), 7.06–6.99 (m), 6.94–6.82 (m), 6.06 (t), 5.94 (t), 5.05 (q), 4.99 (q), 4.56 (q), 3.90 (s), 3.91 (s), 3.82 (s), 3.75 (s), 3.37 (dd), 3.28 (dd), 3.16 (dd), 3.08 (s), 2.99 (dd), 2.82–2.62 (m), 2.76 (s), 2.05–1.74 (m).

Example 21
3-Benzyl-2(S)-(methyl-(2-oxo-2-(3,4,5-trimethoxyphenyl) acetyl)amino)propanoic acid ((7-pyridin-4-ylmethoxy)-1,2,3,4-tetrahydronaphthalen-1(S)-yl) ester (Compound 21):

Compound 21 was prepared according to Examples 4–6, but replacing (S)-Alloc-pipecolic acid with (S)-Alloc-N-methyl-phenylalanine and utilizing Compound 2(S). $^1$H NMR as a mixture of rotomers (500 MHz, CDCl$_3$) d 8.58 (dd), 8.53 (dd), 7.36 (d), 7.31–7.20 (m), 7.14 (s), 7.13–7.08 (m), 7.04 (d), 6.97 (dd), 6.88–6.84 (m), 6.04 (m), 5.18 (t), 5.13 (q), 4.98 (q), 4.53 (q), 3.89 (s), 3.88 (s), 3.78 (s), 3.67 (s), 3.44 (dd), 3.22 (dd), 3.19 (dd), 3.03 (s), 2.98 (dd), 2.82–2.62 (m), 2.78 (s), 2.01–1.87 (m), 1.83–1.73 (m)

Example 22
4-(6-Methyl-5,7-dimethoxyphenyl) butyric acid (Compound 22):

To a solution of 2,4-dimethoxybenzaldehdye (5.1 g, 28.3 mmol) and propanoic triphenylphosphonium bromide (14.4 g, 34.9 mmol) in methylene chloride (40 mL) at 0° C. was added 1.0M potassium t-butoxide in tetrahydrofuran (70 mmol). The reaction was allowed to warm to room temperature and stirred for 2 hr. The reaction was quenched by the addition of 2N hydrochloric acid and extracted with ethyl acetate (2×). The extracts were combined, waashed with brine, dried over anh. magnesium sulfate, filtered and concentrated in vacuo. the residue was chromatographed on silica gel (elution with 5% methanol:methylene chloride) to provide 5.81 grams of a yellow oil. This material was dissolved in ethyl acetate (20 mL), treated with 10% palladium on carbon (581 mg) and hydrogenated at 40 psi. After 12 hr, the hydrogen was replaced with nitrogen, the reaction was filtered and concentrated in vacuo to provide 5.73 g of Compound 22.

Example 23
6-Methyl-5,7-dimethoxy-1,2,3,4-tetrahydronaphthalen-1-one (Compound 23):

To a solution of Compound 22 (5.73 g, 24.07 mmol) and 85% phosphoric acid (2.36 g, 24.07 mmol) in acetonitirle (50 mL) at 50° C. was added trifluoroacetic anhydride (3.5 mL, 25 mmol). After 15 min, the reaction was cooled, diluted with ethyl acetate and washed with water, 10% sodium bicarbonate, brine, dried over anh. magnesium sulfate, filtered and concentrated in vacuo. Chromatography of the residue on silica gel (elution with 5% ethyl acetate:hexanes) provided 3.54 g of Compound 23.

Example 24
6-Methyl-5,7-dipropoxy-1,2,3,4-tetrahydronaphthalen-1-one (Compound 24):

To a solution of Compound 23 (3.54 g, 16.1 mmol) in toulene (50 mL0 was added aluminum chloride (10.7 g, 80.5 mmol) in portions. Once the addition was complete, the mixture was heated to reflux, stirred for 30 min and cooled to 0° C. The reaction was quenched by the addition of 1N hydrochloric aicd and the product extract with ethyl acetate (2×). The extracats were combined, washed with water, brine, dried over anh. magnesium sulfate, filtered and concentrated in vacuo. The residue was passed through a plug of silica gel (elution with 20% ethyl acetate:hexanes) to provide 2.78 g of diol. This material was dissolved in 2-butanone (25 mL), treated with 1-bromopropane (6.6 mL, 72.6 mmol) and powdered potassium carbonate (9.68 g, 72.6 mmol) and heated to reflux. After 12 hr the reaction was cooled, diluted with water and extracted with ethyl acetate (2×). The extracats were combined, washed with water, brine, dried over anh. magnesium sulfate, filtered and concentrated in vacuo. Chromatography of the residue on silica gel (elution with 10% ethyl acetate:hexanes) provided 3.42 g of Compound 24.

Example 25

7-(Pyridin-4-ylmethoxy)-2-pyridin-3-ylmethlene-3,4-dihydro-2H-naphthalen-1-one (Compound 25):

To a solution of Compound 24 (3.42 g, 12.4 mmol) and 3-pyridinecarboxadehyde (1.59 g, 14.9 mmol) in abs. ethanol (25 mL) was added potassium hydroxide (350 mg, 6.2 mmol) and the reaction allowed to stir for 15 min. The reaction was concentrated and the residue dissolved in ethyl acetate washed with water, brine, dried over anh. magnesium sulfate, filtered and concentrated in vacuo. Chromatography of the residue on silica gel (elution with 50% ethyl acetate:hexanes) provided 4.26 g of Compound 25 as an off white solid.

Example 26

6-Methyl-5,7-dipropoxy-2-(pyridin-3-ylmethyl)-1,2,3,4-tetrahydronaphthalen-1-one (Compound 26):

A mixture of Compound 25 (3.96 g, 10.8 mmol) and 10% palladium on carbon (600 mg) in abs. methanol (100 mL) was hydrogenated at 1 atm for 12 hr. The hydrogen was replaced with nitrogen, the reaction was filtered and concentrated in vacuo. Chromatography of the residue on silica gel (elution with 20% ethyl acetate:hexanes) provided 2.72 g of Compound 26.

Examples 27 and 28

Syn-6-Methyl-5,7-dipropoxy-2-(pyridin-3-ylmethyl)-1,2,3,4-tetrahydronaphthalen-1-ol Compound (27) and Anti-6-Methyl-5,7-dipropoxy-2-(pyridin-3-ylmethyl)-1,2,3,4-tetrahydronaphthalen-1-ol (Compound 28):

To a solution of Compound 26 (1.10 g, 2.98 mmol) in abs. methanol (10 mL) was slowly added sodium borohydride (226 mg, 2.98 mmol). After stirring for 1 hr, the reaction was concentrated and the residue partitioned between ethyl acetate and water. The layers were separated and the organic phase was washed with brine, dried over anh. magnesium sulfate, filtered and concentrated in vacuo. Chromatography of the residue on silica gel (elution with 10% ethyl acetate:hexanes) provided 502 mg of Compound 27. Further elution provided 475 mg of Compound 28.

Examples 29A and 29 B 1-(2-Oxo-2-(3,4,5-trimethoxyphenyl)acetyl)piperidine-2(S)-carboxylic acid (7-(pyridin-4-ylmethoxy)-2(R)-(pyridin-3-ylmethyl)-1,2,3,4-tetrahydronaphthalen-1(S)-yl) ester and 1-(2-Oxo-2-(3,4,5-trimethoxyphenyl)-acetyl) piperidine-2(S)-carboxylic acid (7-(pyridin-4-ylmethoxy)-2 (S)-(pyridin-3-ylmethyl)-1,2,3,4-tetrahydronaphthalen-1(R) -yl)ester (Compound 29A and 29B):

Examples 29A and 29B were prepared as described in Examples 4–6, but replacing Compound 2 with Compound 28 to provide a diastereomeric mixture. Chromatography of the mixture on silica gel (elution 10% acetone:hexanes) provided Compound 29A. Further elution provided Compound 29B.

Compound 29A: $^1$H NMR as a mixture of rotomers (500 MHz, CDCl$_3$) d 8.54–8.43 (m), 7.60 (d), 7.41 (s), 7.31 (s), 7.30–7.28 (m), 6.61 (s), 6.57 (s), 5.97 (d), 5.93 (d), 5.40 (d), 4.63 (br d), 4.43 (d), 3.98 (s), 3.97–3.68 (m), 3.93 (s), 3.89 (s), 3.50 (br d), 3.32 (dt), 3.22 (dt), 3.01 (dt), 2.91 (m), 2.78 (dq), 2.56 (quintet), 2.44 (m), 2.23–2.10 (m), 2.17 (s), 1.85–1.71 (m), 1.69–1.49 (m), 1.1 (t), 1.03 (t), 1.00 (t).

Compound 29B: $^1$H NMR as a mixture of rotomers (500 MHz, CDCl$_3$) d 8.49 (s), 8.47 (s), 7.54 (m), 7.36 (s), 7.38–7.21 (m), 6.62 (s), 6.53 (s), 6.03 (d), 5.39 (d), 4.55 (br d), 4.38 (d), 3.96 (s), 3.95 (s), 3.93 (s), 3.90 (s), 3.83 (dt), 3.69 (dt), 3.48 (q), 3.44 (br d), 3.16 (dt), 3.00 9br d), 2.83 (dd), 2.72–2.49 (m), 2.45 (br d), 2.18 (m), 2.15 (s), 2.14 (s), 1.94–1.68 (m), 1.61(m), 1.49 (m), 1.35 (m), 1.20 (t), 1.04 (t), 0.97 (t).

Examples 30A and 30B 1-(2-Oxo-2-(3,4,5-trimethoxyphenyl)acetyl)piperidine-2(S)-carboxylic acid (7-(pyridin-4-ylmethoxy)-2(R)-(pyridin-3-ylmethyl)-1,2,3,4-tetrahydronaphthalen-1(R)-yl) ester and 1-(2-Oxo-2-(3,4,5-trimethoxyphenyl)acetyl) piperidine-2(S)-carboxylic acid (7-(pyridin-4-ylmethoxy)-2 (S)-(pyridin-3-ylmethyl)-1,2,3,4-tetrahydronaphthalen-1(S) -yl) ester (Compound 30A and 30B):

Examples 30A and 30B were prepared as described in Examples 4–6, but replacing Compound 2 with Compound 29 to provide a diastereomeric mixture. Chromatography of the mixture on silica gel (elution 10% acetone:hexanes) provided Compound 30A. Further elution provided Compound 30B.

Compound 30A: $^1$H NMR as a mixture of rotomers (500 MHz, CDCl$_3$) d 8.48 (m), 7.57 (m), 7.37 (s), 7.33–7.27 (m), 7.20 (s), 6.51 (s), 6.49 (s), 5.85 (d), 5.38 (d), 4.60 (br d), 4.39 (d), 3.97 (s), 3.95–3.28 (m), 3.94 (s), 3.87 (s), 3.73 (t), 3.50 (dd), 3.30 (dt), 2.98 (dt), 2.84–2.65 (m), 2.51 (dd), 2.42 (br d), 2.32 (m), 2.17 (t), 1.98 (m), 1.87–1.73 (m), 1.68–1.50 (m), 1.47 (m), 1.09 (t), 1.07 (t), 1.04 (t), 0.99 (t).

Compound 30B: $^1$H NMR as a mixture of rotomers (500 MHz, CDCl$_3$) d 8.49 (m), 8.43 (d), 8.32(d), 7.57 (m), 7.36 (s), 7.35 (s), 7.30–7.25 (m), 7.18 (s), 6.63 (s), 6.48 (s), 6.35 (s), 6.02 (d), 5.87 (d), 5.77 (d), 5.38 (m), 4.66 (br d), 4.44 (d), 3.98–3.67 (m), 3.52 (br d), 3.44 (br d), 3.33 (dt), 3.26 (dt), 3.14 (dt), 3.01 (br d), 2.88–2.49 (m), 2.32 (m), 2.17 (s), 2.16 (s), 2.12 (s), 2.01 (m), 1.87–1.72 (m), 1.68–1.53 (m), 1.09 (t), 1.04(t), 1.02 (t), 0.98 (t).

Example 31

In order to directly determine the neurotrophic activity of compounds described in this invention, the neurite outgrowth assay was carried out with pheochromocytoma PC12 cells as described by Lyons et al.(1994).

PC12 cells are mainatined at 37 degree and 5% CO2 in Dulbecco's modified Eagle's medium (DMEM) suppplemented with 10% heat-inactivated horse serum, 5% heat-inactivated fetal bovine serum (FBS), and 1% glutamate. The cells are then plated at $10^5$ per well in 96 well plates coated with 5 $\mu$g/cm$^2$ rat tail collagen and allowed to attach overnight. The medium is then replaced with DMEM, 2% heat-inactivated horse serum, 1% glutamate, 1–5 ng/ml of NGF (Sigma) and varying concentrations of compound (0.1 nM–10 nM). The background control culture is administered with 105 ng/ml of NGF alone without compound. Positive control cultures are administered with high concentration of NGF (50 ng/ml).

The compounds described in this invention herein cause a significant increase in neurite outgrowth over background control cultures.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A pharmaceutically acceptable composition comprising:
   a) a neurotrophic amount of a compound having the formula (I):

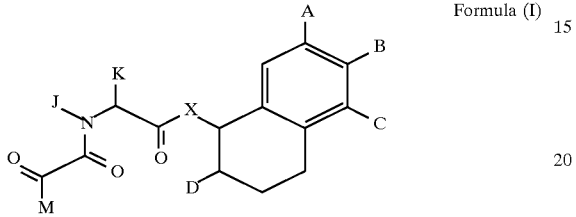

Formula (I)

and pharmaceutically acceptable derivatives thereof, wherein A, B, and C are independently:
hydrogen, (C1–C6)-straight or branched alkyl, O—(C1–C6)-straight or branched alkyl, $(CH_2)_n$—Ar, $Y(CH_2)_n$—Ar or halogen, wherein:
n is 0–4;
Y is O, S, or $NR_1$;
$R_1$, is (C1–C6)-straight or branched alkyl or hydrogen;
wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl;
wherein each Ar optionally contains one to three substituents independently selected from hydrogen, hydroxyl, halogen, nitro, $SO_3H$, trifluoromethyl, trifluoromethoxy, (C1–C6)-straight or branched alkyl, O—(C1–C6)-straight or branched alkyl, O-benzyl, O-phenyl, 1,2-methylenedioxy, carboxyl, morpholinyl, piperidinyl and $NR_2R_3$ or $NR_2R_3$ carboxamides;
wherein $R_2$ and $R_3$ are independently selected from hydrogen, (C1–C5)-straight or branched alkyl or benzyl;
wherein D is selected from hydrogen or $(CH_2)_m$—E, wherein:
E is Ar or $NR_4R_5$;
m=1–3; and
$R_4$ and $R_5$ are independently selected from hydrogen, alkyl (C1–C5 straight or branched)

or $(CH_2)$Ar or can be taken together to form a 5 or 6 membered heterocyclic ring;
wherein X is O or $NR_6$, wherein:
$R_6$ is selected from hydrogen, (C1–C6)-straight or branched alkyl or $(CH_2)_m$—Ar;
m=1–3;
wherein J and K are independently (C1–C6)-straight or branched alkyl or Ar-substituted (C1–C6)-straight or branched alkyl or wherein J and K are taken together to form a five or six membered ring or a five or six membered benzo-fused ring;
wherein M is (C1–C6)-straight or branched alkyl or Ar; and
wherein the stereochemistry at carbon 1 and carbon 2 is R or S;
   b) a neurotropic factor; and
   c) a pharmaceutically suitable carrier.

2. The pharmaceutically acceptable composition according to claim 1, wherein said compound has the formula:

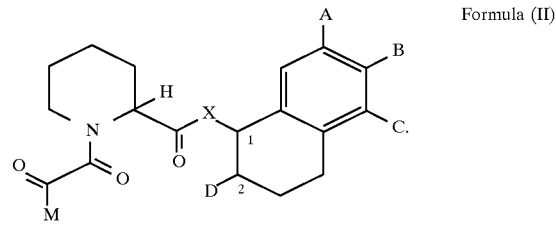

Formula (II)

3. The pharmaceutically acceptable composition according to claim 1, wherein said compound has the formula:

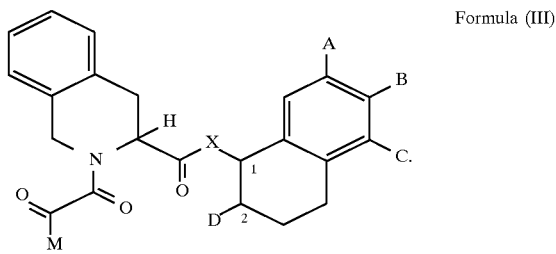

Formula (III)

4. The pharmaceutically acceptable composition according to claim 1, wherein said compound has the formula:

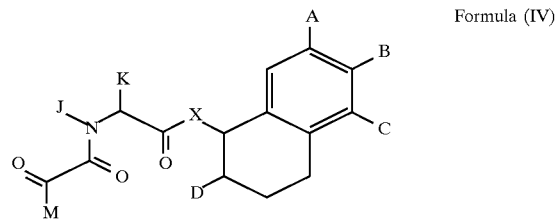

Formula (IV)

wherein
J is methyl or hydrogen; and
K is $(CH_2)_m$—Ar or (C1–C6)-straight or branched alkyl.

5. The pharmaceutically acceptable composition according to claim 4, wherein J is substituted or unsubstituted benzyl.

6. The pharmaceutically acceptable composition according to any one of claims 1 to 5, wherein:
A and C are independently selected from —O—CH₂-4-pyridine, —O-propyl or hydrogen;
B is selected from —O—CH₂-4-pyridine, —O-propyl or hydrogen; and D is selected from —CH$_2$-3-pyridine or hydrogen.

7. The pharmaceutically acceptable composition according to any one of claims 1 to 5, wherein M is 3,4,5-trimethoxyphenyl.

8. The pharmaceutically acceptable composition according to any one of claims 1 to 5, wherein X is selected from oxygen, NH$_2$ or N-benzyl.

9. The pharmaceutically acceptable composition according to claim 1, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotropic factors (CNTF), glial cell-derived neurotropic factor (GDNF), neurotrophin-3 (NT-3) or neurotrophin 4/5 (NT-4/5).

10. The pharmaceutically acceptable composition according to claim 9, wherein said neurotrophic factor is nerve growth factor (NGF).

11. A method for stimulating neurite growth in a patient or in an ex vivo nerve cell comprising the step of administering to said patient or said nerve a neurotrophic amount of a compound having the formula (I):

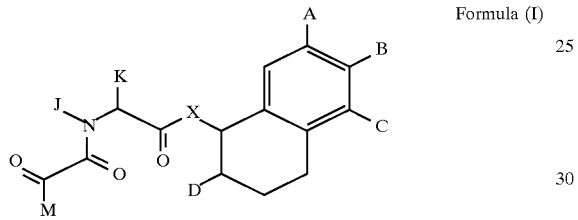

Formula (I)

wherein:
- A, B, and C are independently selected from hydrogen, (C$_1$-C$_6$)-straight or branched alkyl, O—(C$_1$-C$_6$)-straight or branched alkyl, (CH$_2$)$_n$—Ar, Y—(CH$_2$)$_n$—Ar or halogen, wherein:
  - n is 0–4;
  - Y is O, S, or NR$_1$;
  - R$_1$ is (C$_1$-C$_6$)-straight or branched alkyl or hydrogen;
  - each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo furanyl, benzo thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pyridinyl, carbazolyl, acridinyl, phenazinyl, phenothiazinyl or phenoxazinyl; and
  - wherein each Ar optionally contains one to three substituents independently selected from hydrogen, hydroxyl, halogen, nitro, SO$_3$H, trifluoromethyl, trifluoromethoxy, (C1–C6)-straight or branched alkyl, O—(C1–C6)-straight or branched alkyl, O-benzyl, O-phenyl, 1,2-methylenedioxy, carboxyl, morpholinyl, piperidinyl and NR$_2$R$_3$ or NR$_2$R$_3$ carboxamides;
  - wherein R$_2$ and R$_3$ are independently selected from hydrogen, (C1–C5)-straight or branched alkyl or benzyl; D is selected from hydrogen or (CH$_2$)$_m$—E, wherein:
    - E is Ar or NR$_4$R$_5$;
    - m=1–3; and
    - R$_4$ and R$_5$ are independently selected from hydrogen, (C$_1$-C$_5$)-straight or branched alkyl or (CH$_2$)Ar or R$_4$ and R$_5$ are be taken together to form a 5 or 6 membered heterocyclic ring;
- X is O or NR$_6$, wherein:
  - R$_6$ is selected from hydrogen, (C$_1$-C$_6$)-straight or branched alkyl or (CH$_2$)$_m$—Ar;
- J and K are independently (C$_1$-C$_6$)-straight or branched alkyl or Ar-substituted (C$_1$-C$_6$)-straight or branched alkyl or wherein J and K are taken together to form a five or six membered ring which is optionally benzo-fused;
- M is (C$_1$-C$_6$)-straight or branched alkyl or Ar; and
- the stereochemistry at carbon 1 and carbon 2 is R or S.

12. The method according to claim 11, wherein said compound has the formula:

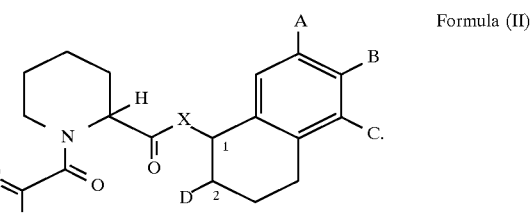

Formula (II)

13. The method according to claim 11, wherein said compound has the formula:

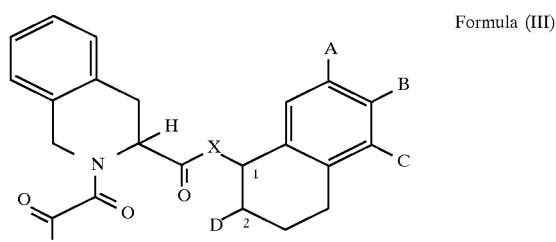

Formula (III)

14. The method according to claim 11, wherein said compound has the formula:

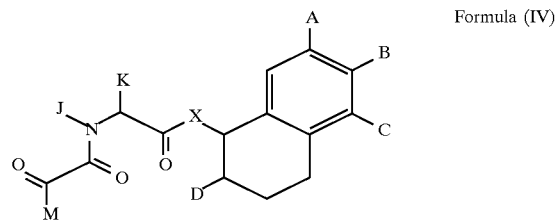

Formula (IV)

wherein J is methyl or hydrogen; and K is (CH$_2$)$_m$—Ar or (C$_1$-C$_6$)-straight or branched alkyl.

15. The method according to claim 14, wherein J is substituted or unsubstituted benzyl.

16. The method according to any one of claims 11–15, wherein:
- A and C are independently selected from —O—CH$_2$-4-pyridine, —O-propyl or hydrogen;
- B is selected from —O—CH$_2$-4-pyridine, —O-propyl or hydrogen; and
- D is selected from —CH$_2$-3-pyridine or hydrogen.

17. The method according to any one of claims 11–15, wherein M is 3,4,5-trimethoxyphenyl.

18. The method according to any one of claims 11–15, wherein X is selected from oxygen, NH$_2$ or N-benzyl.

19. The method according claim 12, wherein said compound is selected from any one of the following compounds:

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl)ester (compound 6);

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(R)-yl)ester (compound 7);

1-(2-oxo-2-(3,4,5-trimethoxyphenyl)-acetyl)-piperidine-2(S)-carboxylic acid 2-((6-pyridin-4-ylmethoxy)-1,2,3,4-tetrahydronaphthalen-1-yl)ester (compound 8):

1-(2-oxo-2-(3,4,5-trimethoxyohenyl)-acetyl)-piperidine-2(S)-carboxylic acid 2-((5-pyridin-4-ylmethoxy)-1,2,3,4-tetrahydronaphthalen-1-yl)ester (compound 9);

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(R)-yl)amide (compound 11A):

1-(2-oxo-2-(3,4,5-trimethoxyphenyl)-acetyl)-piperidine-2(S)-carboxylic acid 2-((7-pyridin-4-ylmethoxy)-1,2,3,4-tetrahydronaphthalen-1(S)-yl)amide (compound 11B);

1-(2-oxo-2-(3,4,5-trimethoxyphenyl)-acetyl)-piperidine-2(S)-carboxylic acid 2-(N-benzyl(7-pyridin-4-ylmethoxy)-1,2,3,4-tetrahydronaphthalen-1(R)-yl)amide (compound 15);

1-(2-oxo-2-(3,4,5-trimethoxyphenyl)-acetyl)-peridine-2(S)-carboxylic acid 2-(N-benzyl(7-pyridin-4-ylmethoxy)-1,2,3,4-tetrahydronaphthalen-1-yl)amide (compound 16);

1-(2-oxo-2-(3,4,5-trimethoxyphenyl)-acetyl)-piperidine-2(S)-carboxylic acid (6-methyl-5,7-dipropoxy-2(R)-(pyridin-3-ylmethyl)-1,2,3,4-tetrahydronaphthalen-1(S)-yl)ester (compound 29A);

1-(2-oxo-2-(3,4,5-trimethoxyphenyl)-acetyl)-piperidine-2(S)-carboxylic acid (6-methyl-5,7-dipropoxy-2(S)-(pyridin-3-ylmethyl)-1,2,3,4-tetrahydronaphthalen-1(R)-yl)ester (compound 29B);

1-(2-oxo-2-(3,4,5-trimethoxyphenyl)-acetyl)-piperidine-2(S)-carboxylic acid (6-methyl-5,7-dipropoxy-2(R)-(pyridin-3-ylmethyl)-1,2,3,4-tetrahydronaphthalen-1(R)-yl)ester (compound 30A); or 1-(2-oxo-2-(3,4,5-trimethoxyphenyl)-acetyl)-piperidine-2(S)-carboxylic acid (6-methyl-5,7-dipropoxy-2(S)-(pyridin-3-ylmethyl)-1,2,3,4-tetrahydronaphthalen-1(S)-yl)ester (compound 30B).

20. The method according to claim 13, wherein said compound is selected from any one of the following compounds:

2-(2-oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(R)-yl)ester (compound 17); or 2-(2-oxo-2-(3,4,5-trimethoxyphenyl)-acetyl)-1,2,3,4-tetrahydroisoquinoline-3(S)-carboxylic acid 2-((7-pyridin-4-ylmethoxy)-1,2,3,4-tetrahydronaphthalen-1(S)-yl)ester (compound 18).

21. The method according to claim 14, wherein said compound is selected from any of the following compounds:

3-benzyl-2(S)-((2-oxo-2-(3,4,5-trimethoxyphenyl)-acetyl)amino)propanoic acid ((7-pyridin-4-ylmethoxy)-1,2,3,4-tetrahydronaphthalen-1(R)-yl)ester (compound 19);

3-benzyl-2(S)-(methyl-(2-oxo-2-(3,4,5-trimethoxyphenyl)-acetyl)amino)propanoic acid ((7-pyridin-4-ylmethoxy)-1,2,3,4-tetrahydronaphthalen-1(R)-yl)ester (compound 20); or 3-benzyl-2(S)-(methyl-(2-oxo-2-(3,4,5-trimethoxyphenyl)-acetyl)amino)propanoic acid ((7-pyridin-4-ylmethoxy)-1,2,3,4-tetrahydronaphthalen-1(S)-yl)ester (compound 21).

22. The method according to claim 11, wherein said compound is administered to a patient and is formulated together with a pharmaceutically suitable carrier into a pharmaceutically acceptable composition.

23. The method according to claim 22, wherein said method is used to treat a patient suffering from Alzheimer's disease, Parkinson's disease, ALS, multiple sclerosis, stroke and ischemia associated with stroke, neural paropathy, other neural degenerative diseases, motor neuron diseases, sciatic crush, peripheral neuropathy, diabetic neuropathy, spinal cord injury or facial nerve crush.

24. The method according to claim 23, comprising the additional step of administering to said patient a neurotrophic factor either as part of a multiple dosage form with said compound or as a separate dosage form.

25. The method according to claim 24, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived eurotrophic factor (BDNF), ciliary neurotropic factors CNTF), glial cell-derived neurotropic factor (GDNF), neurotrophin-3 (NT-3) and neurotrophin 4/5 (NT-4/5).

26. The method according to claim 25, wherein said neurotrophic factor is nerve growth factor (NGF).

27. The method according to any one of claims 23–26, wherein said patient is suffering from diabetes associated peripheral neuropathy.

28. The method according to claim 11, wherein said method is used to stimulate ex vivo nerve regeneration.

29. The method according to claim 28, comprising the additional step of contacting said nerve cell with a neurotrophic factor.

30. The method according to claim 29, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotropic factors (CNTF), glial cell-derived neurotropic factor (GDNF), neurotrophin-3 (NT-3) or neurotrophin 4/5 (NT-4/5).

31. The method according to claim 30, wherein said neurotrophic factor is nerve growth factor (NGF).

* * * * *

UNITED STATES PATENT AND TRADEMARK OFFICE
CERTIFICATE OF CORRECTION

PATENT NO. : 5,811,434
DATED : September 22, 1998
INVENTOR(S) : Robert E. Zelle et al.

Page 1 of 2

It is certified that error appears in the above-identified patent and that said Letters Patent is hereby corrected as shown below:

Cover Page, Item [73], delete "Pharmacueticals" and substitute therefor -- Pharmaceuticals --.

Cover Page, Item [56], delete "WO 96/15101 5/1995" and substitute therefor -- WO 96/15101 5/1996 --.

Cover Page, Item [56], delete "Immunosupressant" and substitute therefor -- Immunosuppressant--.

Cover Page, Item [56], Attorney, Agent, or Firm, delete "Gouindaswamy" and substitute therefor -- Govindaswamy--.

Column 2, line 54 delete "branced" and substitute therefor -- branched --.

Column 3, line 24 delete "is is" and substitute therefor -- is --.

Column 5, Table 1, Compound 30A delete "metthyl" and substitute therefor -- methyl --.

Column 9, line 36 delete "in in" and substitute therefor -- in --.

Column 10, line 52 after "6.64 (d)" insert a comma -- , --.

Column 11, line 27 after "1,2,3,4" insert a hyphen -- - --.

Column 12, line 16 delete "2, 3" and substitute therefor -- 2,3 --.

Column 12, line 53 delete "provide" and substitute therefor -- provided --.

Column 12, line 62 delete "hr,the" and substitute therefor -- hr, the --.

Column 12, line 63 delete "neutalized" and substitute therefor -- neutralized --.

Column 14, line 27 delete "dimethoxybenzaldehdye" and substitute therefor -- dimethoxybenzaldehyde --.

Column 14, line 34 delete "waashed" and substitute therefor -- washed --.

Column 14, line 49 delete "acetonitirle" and substitute therefor -- acetonitrile --.

Column 14, line 66 delete "aicd" and substitute therefor-- acid--.

Column 14, line 67 and column 15, line 9 delete "extracats" and substitute therefor -- extracts --.

Column 16, line 12 delete "9br" and substitute therefor -- (br --.

UNITED STATES PATENT AND TRADEMARK OFFICE
CERTIFICATE OF CORRECTION

PATENT NO. : 5,811,434
DATED : September 22, 1998
INVENTOR(S) : Robert E. Zelle et al.

It is certified that error appears in the above-identified patent and that said Letters Patent is hereby corrected as shown below:

Column 16, line 51 delete "mainatined" and substitute therefor -- maintained --.
Column 16, line 53 delete "suppple-" and substitute therefor -- supple- --.
Column 17, line 30 delete "$R_1$," and substitute therefor -- $R_1$ --.
Column 18, line 16; column 19, line 13; column 19, line 14; column 22, line 37; column 22, line 55; and column 22, line 56 delete "neurotropic" and substitute therefor -- neurotrophic --.
Column 19, line 48 after both occurrences of "benzo" insert -- [b] --.
Column 20, line 4 delete "be".
Column 21, line 12 delete "trimethoxyohenyl" and substitute therefor -- trimethoxyphenyl --.
Column 22, line 35 delete "eurotrophic" and substitute therefor -- neurotrophic --.
Column 22, line 36 delete "neurotropic" and substitute therefor -- neurotrophic --. Delete "CNTF)" and substitute therefor -- (CNTF) --.

Signed and Sealed this

Fifth Day of December, 2000

Attest:

Q. TODD DICKINSON

Attesting Officer

Director of Patents and Trademarks